US010632215B2

(12) United States Patent
Parmegiani

(10) Patent No.: US 10,632,215 B2
(45) Date of Patent: Apr. 28, 2020

(54) DEVICE AND METHOD FOR STERILIZING LIQUID NITROGEN BY ULTRAVIOLET RADIATION

(75) Inventor: Lodovico Parmegiani, San Benedetto del Tronto (IT)

(73) Assignee: NTERILIZER S.R.L., Bologna (IT)

( * ) Notice: Subject to any disclaimer, the term of this patent is extended or adjusted under 35 U.S.C. 154(b) by 429 days.

(21) Appl. No.: 13/140,572

(22) PCT Filed: Dec. 17, 2009

(86) PCT No.: PCT/IB2009/007801
§ 371 (c)(1),
(2), (4) Date: Jun. 17, 2011

(87) PCT Pub. No.: WO2010/070432
PCT Pub. Date: Jun. 24, 2010

(65) Prior Publication Data
US 2012/0102983 A1    May 3, 2012

(30) Foreign Application Priority Data
Dec. 17, 2008  (IT) .............................. PO2008A0019

(51) Int. Cl.
*A61L 2/10*    (2006.01)
(52) U.S. Cl.
CPC .............. *A61L 2/10* (2013.01); *A61L 2202/11* (2013.01)
(58) Field of Classification Search
CPC .... C02F 1/325; C02F 1/32; F17C 2223/0161; F17C 3/085; F17C 2270/0509; F17C 13/006; F17C 2221/014; A61L 2/0047

USPC ..... 62/51.1, 62, 78, 264; 210/748.1, 748.11, 210/748.13
See application file for complete search history.

(56) References Cited

U.S. PATENT DOCUMENTS

| | | | |
|---|---|---|---|
| 2,044,279 A | | 6/1936 | Carmichael |
| 3,228,838 A | * | 1/1966 | Rinfret et al. ................... 34/284 |
| 4,471,225 A | * | 9/1984 | Hillman ......................... 250/436 |
| 4,620,962 A | | 11/1986 | Brodbeck |
| 5,655,681 A | * | 8/1997 | Vogel et al. ............. 220/560.13 |
| 6,264,836 B1 | * | 7/2001 | Lantis ............................ 210/188 |
| 6,972,415 B2 | * | 12/2005 | Schaible et al. .............. 250/436 |
| 2003/0127506 A1 | | 7/2003 | Braun, Jr. |
| 2005/0258108 A1 | * | 11/2005 | Sanford ......................... 210/748 |
| 2006/0011856 A1 | * | 1/2006 | Skaggs .................... 250/455.11 |
| 2011/0127448 A1 | * | 6/2011 | Ben-Shmuel .............. 250/492.1 |

FOREIGN PATENT DOCUMENTS

| | | |
|---|---|---|
| DE | 972 572 C | 8/1959 |
| IT | 1123509 | 4/1986 |
| WO | WO 20071025376 A | 3/2007 |
| WO | WO 2007/051276 | 5/2007 |

* cited by examiner

*Primary Examiner* — Joseph F Trpisovsky
(74) *Attorney, Agent, or Firm* — McGlew and Tuttle, P.C.

(57) ABSTRACT

Described are a device and a method for rapidly sterilizing liquid nitrogen in a container using ultraviolet radiation irradiated for a predetermined length of time based on the temperature measured by a sensor and on the minimum dose of radiation necessary to kill micro-organisms resistant to liquid nitrogen.

20 Claims, 3 Drawing Sheets

DEVICE AND METHOD FOR STERILIZING LIQUID NITROGEN BY ULTRAVIOLET RADIATION

TECHNICAL FIELD

This invention relates to a device and a method for the rapid sterilization of liquid nitrogen of the type used, for example, in processes for cryogenically preserving biological material, in cryotherapy and in molecular gastronomy.

PRIOR ART

As is known, liquid nitrogen is obtained by compressing gaseous nitrogen, which is very common in nature, (it makes up 79% of the Earth's atmosphere) and has a very low boiling point (−195.82° C.).

In its practical applications, when released, liquid nitrogen evaporates and absorbs large quantities of heat, making it very effective for use as a coolant.

Although liquid nitrogen has a low particulate count and a low microbial content (in nature very few micro-organisms are able to survive at temperatures around −195° C.), the need to guarantee the absolute sterility of nitrogen is at present still felt as a problem in view of its critical applications in medicine and in the food industry.

To date, many methods are known for obtaining sterile liquid nitrogen at the time of production and companies that supply liquid nitrogen can certify the type of purity of the liquid nitrogen supplied. Owing to the particular composition of this liquid, however, it is not possible to seal the containers used to transport it and consequently it is not possible to guarantee and certify the sterility of the liquid nitrogen before it is actually used by the end user.

Usually, liquid nitrogen is transported from the manufacturer to the end user (hospital, cryobiology laboratory, medical centre, and so on) in pressurized containers and is deposited in specific cryogenic containers that come in various sizes and can contain anywhere from a few litres to several hundred litres. Very often, between the time of leaving the manufacturer to the time of reaching the end user, the liquid nitrogen passes through several hands (subcontract gas suppliers and/or forwarding agents), exposing the liquid nitrogen to further risks of contamination (during transfers to different cryogenic containers used for its transportation).

Furthermore, incorrect sanitizing or safety procedures during handling of potentially infected biological material in the hospital, laboratory or medical centre where the cryogenic container is located can also lead to nitrogen contamination.

At present, the use of ultraviolet radiation to sterilize surgical material, work tops and water or other liquids is known.

In particular, the use of ultraviolet radiation for sterilizing liquids in general is described in Italian patent publication IT1123509, which discloses an infeed manifold and a conveyor manifold which subject the liquid to a constant pressure.

The features of this solution, however, are applicable to systems for sterilizing liquids similar in composition to water and are difficult to apply to liquids such as liquid nitrogen which evaporate rapidly.

U.S. Pat. No. 2,044,279 describes a method of purifying carbon dioxide using ultraviolet radiation.

U.S. Pat. No. 4,620,962, on the other hand, relates specifically to the sterilization of liquid nitrogen but involves ultrafiltration and UV irradiation of nitrogen in the gaseous state, obtained by evaporating the liquid nitrogen, and then compressing the gaseous nitrogen to reliquefy it. It is therefore a complex process and does not enable the nitrogen to be sterilized directly in the liquid state.

US patent publication 2003/0127506 describes a mailbox comprising ultraviolet lamps for producing UV-C radiation and ozone. The radiation destroys pathogens on the surface of parcels and air circulating within the mailbox allows the ozone to penetrate the parcels to contact the contents and destroy pathogens on the parcel contents.

Patent document WO 2007/051276 regards a wand-type UV radiation sterilizing wand that includes a housing having an aperture and a source of UV radiation mounted within the housing positioned for emitting UV radiation through the aperture.

The latter devices described are obviously unsuitable for sterilizing liquid nitrogen which requires special containers and is characterized by a rapid evaporation rate.

Thus, prior art leaves unsolved, in particular, the technical problem of microbial and viral contamination of biological samples preserved in liquid nitrogen by other samples stored in the same cryogenic container or by the liquid nitrogen itself.

It is therefore possible for the contaminated nitrogen to infect a biological sample through direct contact with it, for example when cells or tissues are frozen or in the case of samples that are cryogenically preserved in bags or other improperly sealed or damaged devices. Moreover, the contaminated nitrogen may come into direct contact with skin lesions during cryotherapy treatments, thus infecting the patient directly.

The need is therefore felt for a device and a method for sterilizing liquid nitrogen before it evaporates.

This invention is therefore applicable to the laboratory, medical and culinary fields where liquid nitrogen must be sterilized immediately before its use as a cryogenic liquid.

More specifically, the invention proposes in particular to sterilize the nitrogen rapidly and directly in its liquid state in the following fields:

Cryopreservation

For sterilizing liquid nitrogen used to fill the specially designed cryogenic containers (Dewars) for the cryopreservation and long-term storage of biological—including human—cells and tissues. For sterilizing liquid nitrogen used in ultra rapid cell cooling techniques, particularly those where the nitrogen comes into direct contact with the cells (vitrification with open system). For sterilizing liquid nitrogen used for cryogenically preserving organs to be transplanted.

Cryotherapy

For sterilizing liquid nitrogen to be used in medical treatments: cryotherapy techniques (for example in proctology or dermatology).

Molecular Gastronomy

For sterilizing liquid nitrogen used in culinary preparations (molecular gastronomy or liquid nitrogen cooking); in effect, it is becoming more and more common for dishes to be prepared by direct immersion of the food in liquid nitrogen (for example, vitrification of olive oil or instant ice cream).

DISCLOSURE OF THE INVENTION

The aim of this invention is therefore to propose a device and a method for rapidly sterilizing liquid nitrogen which are at once simple and effective.

This aim is achieved by a sterilization device and a sterilization method according to the appended claims, based on irradiation with ultraviolet rays.

A first advantage of the invention lies in the fact the device according to the invention, in its preferred embodiment, is easy to use, occupies little space and is applicable in a wide variety of fields where the use of sterile liquid nitrogen is essential or appropriate.

In particular, in the field of cryopreservation the invention has made it possible to achieve rapid freezing of biological material with a high degree of sterility assurance.

Yet another advantage is the possibility of applying the device to widely available commercial containers.

These and other advantages will be better understood from the following description with reference to the accompanying drawings illustrating preferred non-limiting embodiments of the invention.

PREFERRED EMBODIMENT OF THE INVENTION

Figure 1:
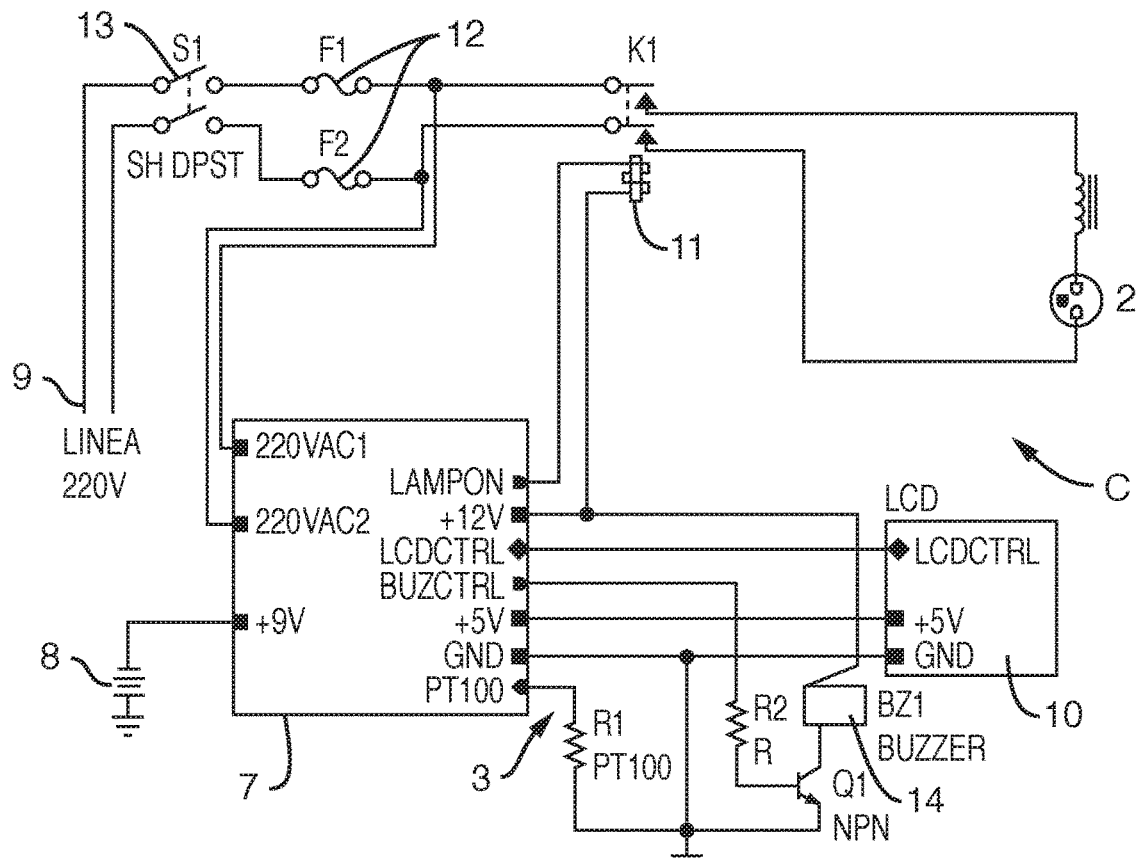
FIG. 1 shows the electrical circuit diagram for a sterilizing device according to the invention.

With reference to FIG. 1, a liquid nitrogen sterilizing device according to the invention comprises a circuit C which includes:
- a UV-C radiation source 2 in the form, for example, of a germicidal lamp;
- a sensor 3, for example a PT100 thermocouple for measuring the temperature in the immediate vicinity of the lamp 2;
- a control 7 equipped with a timer for activating the lamp 2 and programmed with one or more activation times predetermined according to criteria linked to the efficiency of the sterilization process, as well as the amount of nitrogen to be sterilized and the physical properties of the system in which the nitrogen is placed.

The circuit C is powered from a mains power supply 9 through switches 13 and fuses 12, and also comprises:
- a unit (not illustrated) for input of commands;
- a display unit, preferably an LCD 10;
- a rechargeable battery 8 for the control 7;
- a relay 11 for controlling the lamp 2;
- an audible alarm 14.

Advantageously, the control 7 is set to activate the alarm 14 upon the occurrence of certain conditions such as, for example, a decrease in the temperature measured by the probe 3 to below a minimum threshold value in order to keep the UV-C lamp at a suitable efficiency level and to avoid damage to it.

In effect, in terms of irradiated power per surface area unit, the efficiency of germicidal lamps currently available drops rapidly at temperatures under 40° C.

The lamp 2 must therefore be placed at a suitable distance from the liquid nitrogen and preferably thermally insulated from it.

Under these conditions, the probe 3 measures a temperature that is processed by the control 7 and placed in relation with other significant parameters such as the quantity of nitrogen present, the material the liquid nitrogen container is made of and the liquid nitrogen evaporation rate.

Based on the processing performed, the control 7, through the timer, activates the lamp 2 for the time required to emit at least the dose of radiation necessary to destroy the microorganisms resistant to liquid nitrogen.

Figure 2:
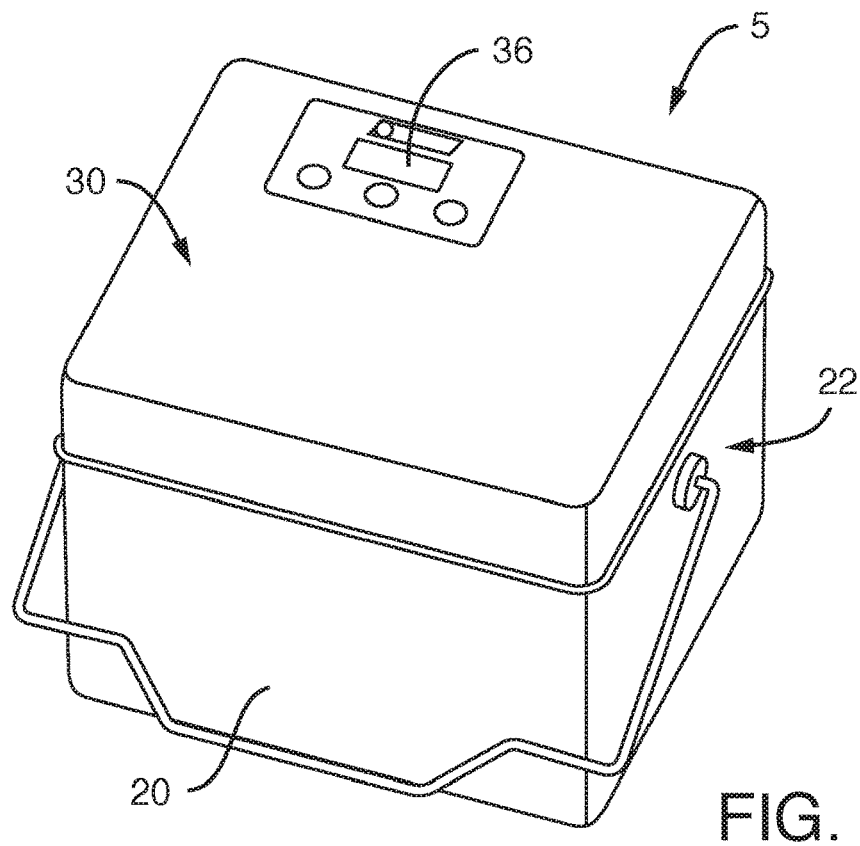
FIG. 2 shows an overall view of a container for sterilizing liquid nitrogen according to the invention.
Figure 3:
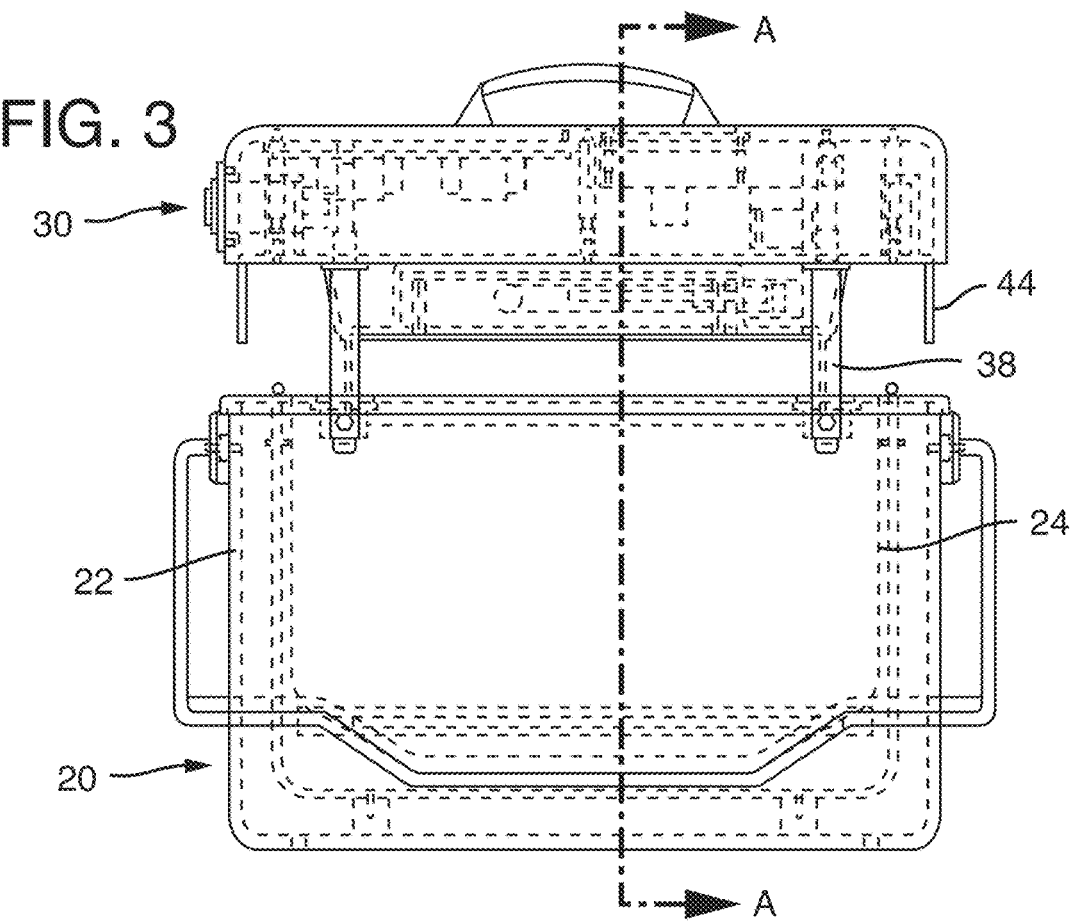
FIG. 3 shows a front view of the container of FIG. 2.
Figure 4:
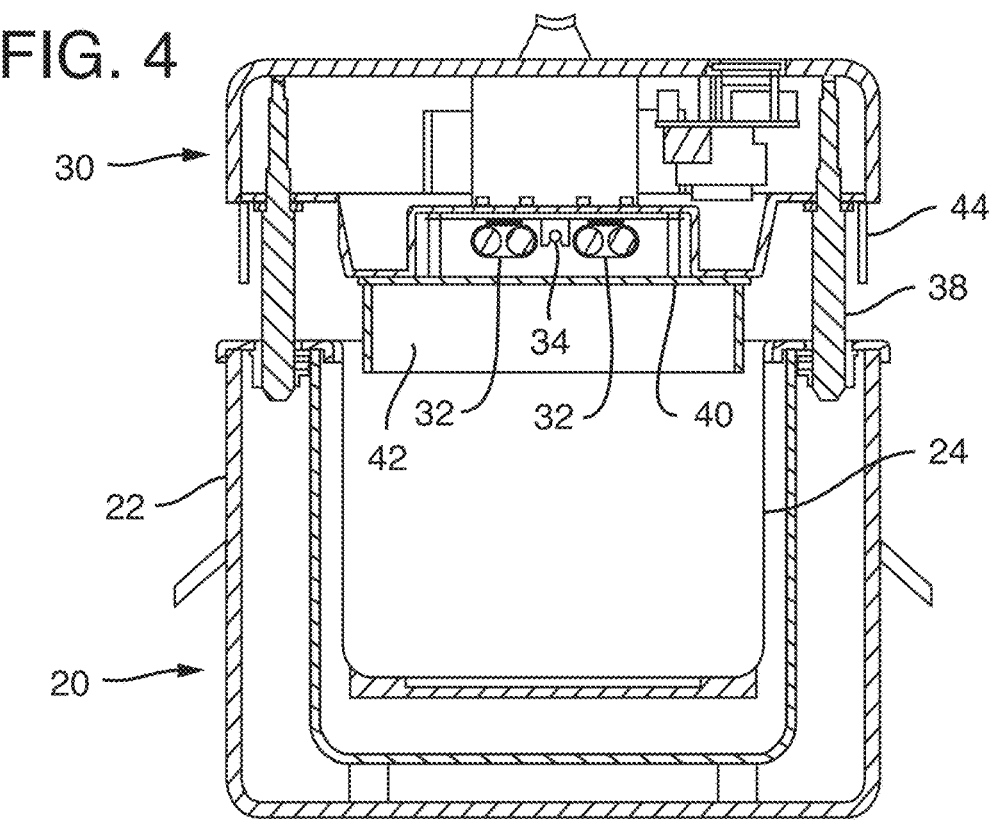
FIG. 4 is a cross section of the container along the line A-A shown in FIG. 3.

FIGS. 2 to 4 illustrate a preferred embodiment of a sterilizing device S according to the invention.

The device comprises a container 20 and a lid 30.

In particular, the container 20 comprises a thermally insulating outer casing 22 and a removable inner tank 24, made of stainless steel, for the liquid nitrogen.

Preferably, the tank 24 has a capacity of 2 to 5 litres of liquid nitrogen and is especially designed to limit heat loss and to guarantee slow evaporation of the nitrogen, thus facilitating the sterilization process.

The circuit C described schematically above is housed under the lid 30 and comprises two UV-C germicidal lamps 32, the temperature sensor 34 and the display 36.

To prevent the temperature of the lamps from falling below the programmed minimum threshold value, spacers 38 are provided to keep the lid raised from the container 20. The lamps are also protected by a piece of quartz glass 40.

Screens 42, 44 are also advantageously provided to prevent leakage of UV radiation reflected by the tank 24.

During use, the non-sterile liquid nitrogen is poured into the tank 24, the lid 30 is placed on the container 20 and the sterilization process begins by activating the UV-C lamps as described above.

A container for sterilizing nitrogen as described above is particularly useful in tissue and cell vitrification processes.

Indeed, when sterilization has been completed, the vitrification process can be performed directly in the tank 24. The nitrogen that comes into direct contact with the biological material is sterile and also renders safe processes for the vitrification of human cells (ovocytes and embryos) using open supports (for example Cryotops or Cryoleaf) without any risk of contaminating the sample.

As stated, the invention contemplates calculating the minimum irradiation time necessary to destroy the micro-organisms resistant to liquid nitrogen; the calculation takes into account that the rate at which the micro-organisms are destroyed (sterilization) is directly proportional to the quantity of liquid nitrogen to be sterilized and depends on the physical properties of the container in which the nitrogen is located.

The method according to the invention also takes into account that the liquid nitrogen released in a container absorbs large quantities of heat and evaporates and that it is desirable to calculate irradiation times in such a way as to complete irradiation before the nitrogen evaporates completely.

Since the rate at which the micro-organisms are killed depends on the efficiency of the UV-C irradiation system which is in turn inversely proportional to the temperature at which the irradiation system operates, the method according to the invention also contemplates a step of checking the efficiency of the system by measuring the temperature in the vicinity of the bulb so as to maintain conditions of maximum efficiency even in the presence of the highly refrigerating effect induced by the evaporation of the liquid nitrogen.

This method of sterilizing liquid nitrogen is therefore based on emitting at least a minimum dose of UV radiation necessary to kill micro-organisms that can survive at the boiling point of nitrogen (−195.82° C.). This dose is preferably irradiated rapidly, within a short time interval, before the liquid nitrogen evaporates completely and so as to prevent reduction of lamp efficiency.

Figure 5:
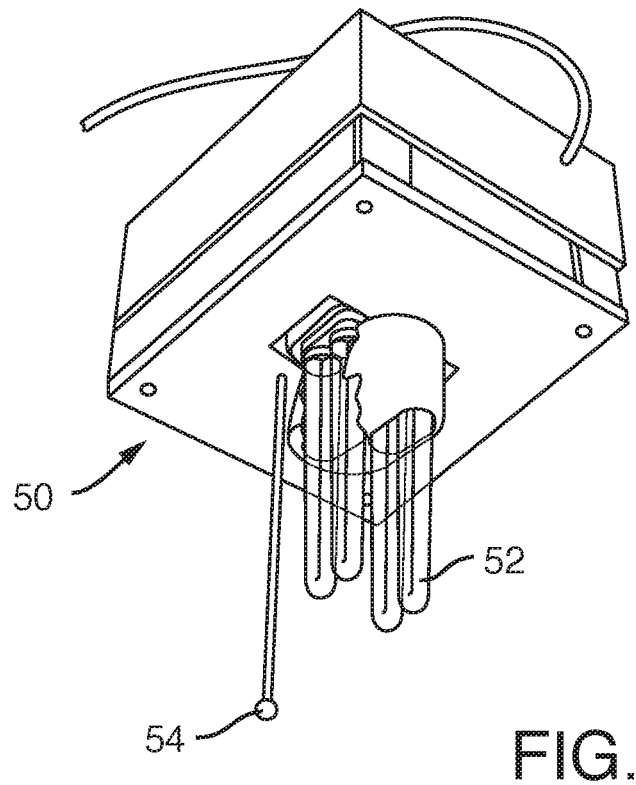
FIGS. 5 and 6 show a prototype of a closing device according to the invention and its schematic application to dewar liquid nitrogen containers.
Figure 6:
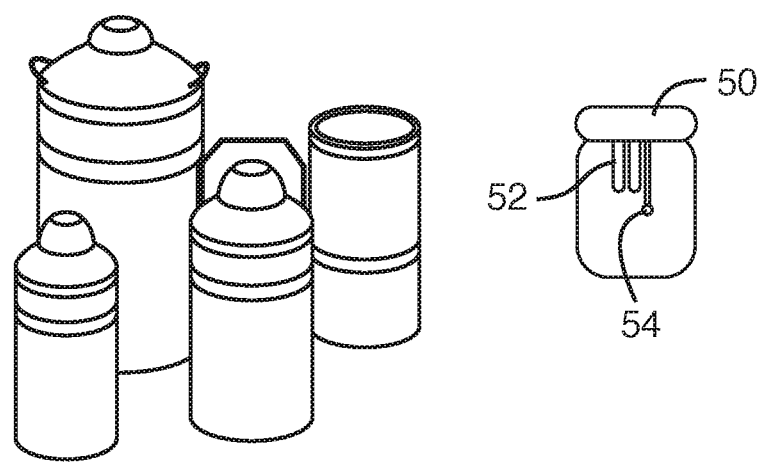

FIGS. 5 and 6 show a prototype of a closing device according to the invention and its schematic application to dewar liquid nitrogen containers.

The closing device 50 is shaped in such a way that it can be used as a "universal sterilizing plug" for commercially available cryogenic containers. It comprises a circuit C, as described above, equipped with two UV-C lamps 52 and an adjacent temperature sensor 54.

The device S can be applied to both "open dewars" (small cryogenic containers for up to 5-6 litres of liquid nitrogen) and large dewars for transporting nitrogen and storing samples (cryobanks).

Further, the device 50 sterilizes both the liquid nitrogen and the inside of the container so that the liquid nitrogen is ready for use when required, for example in cryobiology, cryotherapy or molecular gastronomy.

The invention claimed is:

1. A device for rapidly sterilizing liquid nitrogen using ultraviolet radiation, the device comprising:
   a container open on an upper part thereof;
   a lid connected to said container, said lid being kept in a raised position from the container and the lid housing at least one UV radiation lamp irradiating inside the container;
   a sensor for monitoring a temperature of the lamp;
   a control means operatively connected to the sensor and said UV radiation lamp for activating the UV radiation lamp such that said UV radiation lamp irradiates for a set length of time based on the temperature measured by the sensor and based on a minimum dose of radiation necessary to destroy micro-organisms resistant to liquid nitrogen, wherein said minimum dose irradiation time is calculated as a function of an evaporation rate of the liquid nitrogen in the container.

2. The device according to claim 1, wherein the container comprises a thermally insulating outer casing and a removable inner tank, made of stainless steel, for the liquid nitrogen, and wherein said lid houses the temperature sensor and the control means.

3. The device according to claim 2, wherein the temperature sensor is located near the at least one UV radiation lamp.

4. The device according to claim 3, wherein the lid is kept in the raised position from the container by spacers and the at least one UV radiation lamp is protected by a piece of quartz glass.

5. The device according to claim 4, wherein screens are provided for preventing leakage of UV radiation reflected by the tank.

6. The device according to claim 1, wherein the at least one UV radiation lamp is a UV-C lamp that irradiates at 253.7 nm.

7. The device according to claim 1, wherein the lid is mounted to said container such that said lid is located at a spaced location from said container to define a space between said container and said lid, wherein at least evaporated liquid nitrogen exits said container via at least said space.

8. The device according to claim 1, wherein the lid is mounted to said container such that said lid is located at a spaced location from said container to define a space between said container and said lid, said container comprising an inner container surface defining at least a portion of a container inner space, said container inner space comprising said liquid nitrogen, said at least one UV radiation lamp being located at a spaced location from said liquid nitrogen.

9. The device according to claim 1, wherein said lid is located at a spaced location from said container in said raised position, said lid being free of contact with said container in said raised position.

10. The device according to claim 1, wherein the lid is always maintained at a spaced location from the container when the UV radiation lamp is activated to emit UV radiation.

11. A method of sterilizing liquid nitrogen by UV irradiation,
    the method comprising the following steps:
    providing a container having an opening on an upper part thereof, wherein liquid nitrogen is stored in said container;
    providing a lid connected to said container such that said lid is maintained in a raised position above the opening of said container;
    providing a UV radiation lamp housed in said lid;
    determining a minimum UV dose necessary to kill micro-organisms located in the container or in the liquid nitrogen;
    measuring a temperature in a vicinity of the lamp;
    calculating an irradiating time as a function of the temperature measured and the minimum dose determined;
    irradiating the liquid nitrogen for the irradiation time calculated.

12. The method according to claim 11, wherein the minimum dose irradiation time is calculated as a function of an evaporation rate of the liquid nitrogen in the container.

13. The method according to claim 11, wherein said minimum dose irradiation time is calculated as a function of an evaporation rate of the liquid nitrogen in the container.

14. The method according to claim 11, wherein said lid is located at a spaced location from said container to define a space between said container and said lid, wherein at least evaporated liquid nitrogen exits said container via at least said space.

15. The method according to claim 11, wherein said lid is located at a spaced location from said container to define a space between said container and said lid, said container comprising an inner container surface defining at least a portion of a container inner space, said container inner space comprising said liquid nitrogen.

16. The method according to claim 11, wherein said lid is located at a spaced location from said container in said raised position, said lid being free of contact with said container in said raised position.

17. A process for rapidly freezing biological material using liquid nitrogen, the process comprising:
    providing a UV radiation lamp;
    providing liquid nitrogen in a container having an opening on an upper part thereof, said container comprising a lid connected thereto such that said lid is maintained in a raised position above said opening of said container;
    determining a minimum UV dose necessary to kill micro-organisms located in the container or in the liquid nitrogen;
    measuring a temperature in a vicinity of the lamp;
    calculating an irradiating time as a function of the temperature measured and the minimum dose determined;

irradiating the liquid nitrogen with said lamp for the irradiation time calculated to form sterilized liquid nitrogen;

freezing biological material with said sterilized liquid nitrogen.

18. The process according to claim 17, wherein said minimum dose irradiation time is calculated as a function of an evaporation rate of the liquid nitrogen in the container.

19. The process according to claim 17, wherein said lid is located at a spaced location from said container to define a space between said container and said lid, wherein at least evaporated liquid nitrogen exits said container via at least said space.

20. The process according to claim 17, wherein said lid is located at a spaced location from said container to define a space between said container and said lid, said container comprising an inner container surface defining at least a portion of a container inner space, said container inner space receiving said liquid nitrogen.

* * * * *